(12) United States Patent
Yan et al.

(10) Patent No.: US 8,900,630 B2
(45) Date of Patent: *Dec. 2, 2014

(54) MICROCAPSULES HAVING MULTIPLE SHELLS AND METHOD FOR THE PREPARATION THEREOF

(75) Inventors: Nianxi Yan, Halifax (CA); Yulai Jin, Battle Creek, MI (US)

(73) Assignee: DSM Nutritional Products, Kaiseraugst (CH)

(*) Notice: Subject to any disclaimer, the term of this patent is extended or adjusted under 35 U.S.C. 154(b) by 102 days.

This patent is subject to a terminal disclaimer.

(21) Appl. No.: 13/009,418

(22) Filed: Jan. 19, 2011

(65) Prior Publication Data

US 2011/0111020 A1  May 12, 2011

Related U.S. Application Data

(63) Continuation of application No. 12/642,303, filed on Dec. 18, 2009, now abandoned, which is a continuation of application No. 10/497,290, filed as application No. PCT/CA03/01699 on Nov. 4, 2003, now abandoned.

(60) Provisional application No. 60/423,363, filed on Nov. 4, 2002.

(51) Int. Cl.
| | | |
|---|---|---|
| A61K 9/50 | (2006.01) | |
| A23P 1/04 | (2006.01) | |
| B05D 7/26 | (2006.01) | |
| B01J 13/22 | (2006.01) | |
| A23L 1/22 | (2006.01) | |
| A23L 1/00 | (2006.01) | |
| B01J 13/10 | (2006.01) | |
| A23L 1/30 | (2006.01) | |

(52) U.S. Cl.
CPC ............ *A61K 9/5015* (2013.01); *A61K 9/5073* (2013.01); *A61K 9/5084* (2013.01); *B01J 13/22* (2013.01); *A61K 9/5057* (2013.01); *A23L 1/22016* (2013.01); *A23L 1/0029* (2013.01); *A23V 2002/00* (2013.01); *B01J 13/10* (2013.01); *A61K 9/5089* (2013.01); *A23L 1/3008* (2013.01)
USPC ........... 424/456; 424/436; 424/489; 424/492; 428/402.2; 428/402.21; 428/402.24; 426/89; 426/103; 426/285

(58) Field of Classification Search
USPC ......... 428/402–402.24, 403, 404, 407, 321.1, 428/474.4; 427/389.9, 213.3–213.36, 331, 427/212, 213–213.36, 483, 256; 264/4–4.7, 264/534, 5, 41; 523/206, 213; 525/523, 525/565; 435/68.1, 283.1, 307.1
See application file for complete search history.

(56) References Cited

U.S. PATENT DOCUMENTS

| | | |
|---|---|---|
| 2,800,457 A | 7/1957 | Green et al. |
| 2,800,458 A | 7/1957 | Green |

(Continued)

FOREIGN PATENT DOCUMENTS

| | | |
|---|---|---|
| CA | 2318539 A1 | 7/1999 |
| CA | 2447002 | 4/2003 |

(Continued)

OTHER PUBLICATIONS

Office Action for U.S. Appl. No. 11/988,320 dated Sep. 1, 2011.

(Continued)

*Primary Examiner* — James J Seidleck
*Assistant Examiner* — S. Camilla Pourbohloul
(74) *Attorney, Agent, or Firm* — Meunier Carlin & Curfman, LLC

(57) ABSTRACT

Single-core and multi-core microcapsules are provided, having multiple shells, at least one of which is formed of a complex coacervate of two components of shell materials. The complex coacervate may be the same or different for each shell. Also provided are methods for making the microcapsules.

11 Claims, 9 Drawing Sheets

(56) References Cited

U.S. PATENT DOCUMENTS

| | | | |
|---|---|---|---|
| 3,041,289 A * | 6/1962 | Katchen et al. | 426/415 |
| 3,179,600 A | 4/1965 | Brockett | |
| 3,190,837 A | 6/1965 | Brynko | |
| 3,526,682 A | 9/1970 | Timreck | |
| 3,697,437 A | 10/1972 | Fogel et al. | |
| 4,010,038 A | 3/1977 | Iwasaki et al. | |
| 4,217,370 A | 8/1980 | Rawlings et al. | |
| 4,219,439 A | 8/1980 | Miyake et al. | |
| 4,222,891 A | 9/1980 | Okimoto et al. | |
| 4,232,084 A | 11/1980 | Tate | |
| 4,273,672 A | 6/1981 | Vassiliades | |
| 4,442,051 A | 4/1984 | Rowe et al. | |
| 4,485,172 A | 11/1984 | Gierhart | |
| 4,670,247 A | 6/1987 | Scialpi | |
| 4,695,466 A | 9/1987 | Morishita et al. | |
| 4,744,933 A | 5/1988 | Rha et al. | |
| 4,749,620 A | 6/1988 | Rha et al. | |
| 4,808,408 A | 2/1989 | Baker et al. | |
| 4,861,627 A | 8/1989 | Mathiowitz et al. | |
| 4,867,986 A | 9/1989 | Desai et al. | |
| 4,891,172 A | 1/1990 | Matsushita et al. | |
| 4,895,725 A | 1/1990 | Kantor et al. | |
| 4,923,855 A | 5/1990 | Jensen | |
| 4,946,624 A * | 8/1990 | Michael | 510/101 |
| 4,954,492 A | 9/1990 | Jensen | |
| 4,963,367 A | 10/1990 | Ecanow | |
| 5,013,569 A | 5/1991 | Rubin | |
| 5,035,896 A | 7/1991 | Apfel et al. | |
| 5,051,304 A | 9/1991 | David et al. | |
| 5,059,622 A | 10/1991 | Sears | |
| 5,130,061 A | 7/1992 | Cornieri et al. | |
| 5,156,956 A | 10/1992 | Motoki | |
| 5,194,615 A | 3/1993 | Jensen | |
| 5,204,029 A | 4/1993 | Morgan et al. | |
| 5,330,778 A | 7/1994 | Stark | |
| 5,356,636 A | 10/1994 | Schneider | |
| 5,378,413 A | 1/1995 | Mihm et al. | |
| 5,428,014 A | 6/1995 | Labroo | |
| 5,456,985 A | 10/1995 | Zgoulli et al. | |
| 5,573,934 A | 11/1996 | Hubbell et al. | |
| 5,603,952 A | 2/1997 | Soper | |
| 5,603,961 A | 2/1997 | Suzuki et al. | |
| 5,670,209 A | 9/1997 | Wyckoff | |
| 5,700,397 A | 12/1997 | Maeda et al. | |
| 5,759,599 A | 6/1998 | Wampler et al. | |
| 5,766,637 A | 6/1998 | Shine et al. | |
| 5,780,056 A | 7/1998 | Akamatsu et al. | |
| 5,788,991 A | 8/1998 | Nastke et al. | |
| 5,827,531 A | 10/1998 | Morrison et al. | |
| 5,855,826 A | 1/1999 | Lee et al. | |
| 5,872,140 A | 2/1999 | Hesse et al. | |
| 5,993,851 A | 11/1999 | Foldvari | |
| 5,997,863 A | 12/1999 | Zimmermann | |
| 6,019,998 A | 2/2000 | Nomoto et al. | |
| 6,020,200 A | 2/2000 | Enevol | |
| 6,039,901 A | 3/2000 | Soper | |
| 6,063,820 A | 5/2000 | Cavazza | |
| 6,103,378 A | 8/2000 | Yao et al. | |
| 6,106,875 A | 8/2000 | Soper et al. | |
| 6,221,401 B1 | 4/2001 | Zasadzinski et al. | |
| 6,234,464 B1 | 5/2001 | Krumbholz et al. | |
| 6,274,174 B1 | 8/2001 | Hom-ma et al. | |
| 6,300,377 B1 | 10/2001 | Chopra | |
| 6,325,951 B1 | 12/2001 | Soper et al. | |
| 6,328,995 B1 | 12/2001 | Bewert et al. | |
| 6,365,176 B1 | 4/2002 | Bell et al. | |
| 6,417,233 B1 | 7/2002 | Sears et al. | |
| 6,441,050 B1 | 8/2002 | Chopra | |
| 6,482,433 B1 | 11/2002 | DeRoos et al. | |
| 6,500,463 B1 | 12/2002 | van Lengerich | |
| 6,528,165 B2 | 3/2003 | Chandler | |
| 6,534,091 B1 | 3/2003 | Garces et al. | |
| 6,534,094 B2 | 3/2003 | Moyano et al. | |
| 6,534,926 B1 | 3/2003 | Miller et al. | |
| 6,544,926 B1 | 4/2003 | Bodmer et al. | |
| 6,630,157 B1 | 10/2003 | Horrobin et al. | |
| 6,652,891 B2 | 11/2003 | Selzer | |
| 6,969,530 B1 | 11/2005 | Curtis et al. | |
| 6,972,592 B2 | 12/2005 | Benware | |
| 6,974,592 B2 | 12/2005 | Yan et al. | |
| 7,727,629 B2 | 6/2010 | Yan | |
| 8,039,030 B2 | 10/2011 | Abril et al. | |
| 2002/0031553 A1 | 3/2002 | Moyano et al. | |
| 2003/0044380 A1 | 3/2003 | Zhu et al. | |
| 2003/0078617 A1 | 4/2003 | Schwartz et al. | |
| 2003/0091654 A1 | 5/2003 | Katz et al. | |
| 2003/0133886 A1 | 7/2003 | Smith et al. | |
| 2003/0193102 A1 * | 10/2003 | Yan | 264/4.1 |
| 2004/0106591 A1 | 6/2004 | Pacioretti et al. | |
| 2005/0019416 A1 | 1/2005 | Yan | |
| 2005/0067726 A1 * | 3/2005 | Yan et al. | 264/4.1 |
| 2005/0118285 A1 | 6/2005 | Lacoutiere | |
| 2005/0249952 A1 * | 11/2005 | Vasishtha et al. | 428/402.24 |
| 2007/0027028 A1 | 2/2007 | Pears et al. | |
| 2007/0059340 A1 | 3/2007 | Bello et al. | |
| 2007/0078071 A1 | 4/2007 | Lee | |
| 2007/0141211 A1 | 6/2007 | Kolar et al. | |
| 2007/0224216 A1 | 9/2007 | Teas | |
| 2009/0274791 A1 | 11/2009 | Mattson | |
| 2010/0055281 A1 | 3/2010 | Barrow | |
| 2010/0173002 A1 | 7/2010 | Yulai et al. | |

FOREIGN PATENT DOCUMENTS

| | | |
|---|---|---|
| DE | 1035319 | 7/1958 |
| EA | 200800269 | 6/2006 |
| EP | 0301777 | 2/1989 |
| EP | 0416575 | 3/1991 |
| EP | 0426428 | 5/1991 |
| EP | 0434760 | 1/1994 |
| EP | 0782833 | 7/1997 |
| EP | 0856355 | 8/1998 |
| EP | 1116516 | 7/2001 |
| EP | 0821881 | 9/2001 |
| EP | 0644771 | 8/2002 |
| EP | 1237423 | 9/2002 |
| EP | 0982038 | 1/2003 |
| EP | 03773376.3-2112 | 11/2003 |
| EP | 0745670 | 6/2004 |
| EP | 1430947 A1 | 6/2004 |
| EP | 1357977 B1 | 7/2004 |
| EP | 0897970 | 9/2004 |
| EP | 06020381.7 | 9/2006 |
| GB | 1198412 | 7/1970 |
| GB | 2091286 | 7/1982 |
| GB | 2115768 | 9/1983 |
| JP | 5394273 A | 8/1978 |
| JP | 5828234 | 2/1983 |
| JP | 58149645 | 9/1983 |
| JP | 61172807 | 8/1986 |
| JP | 1148338 | 6/1989 |
| JP | 02086743 | 3/1990 |
| JP | 5292899 | 11/1993 |
| JP | 2002/028473 | 1/2002 |
| JP | 2003-583137 | 4/2003 |
| JP | 2005/522313 | 7/2005 |
| JP | 2006/506410 | 2/2006 |
| WO | WO 91/06287 | 5/1991 |
| WO | WO 92/11083 | 7/1992 |
| WO | WO 97/13416 | 4/1997 |
| WO | WO 97/40701 | 11/1997 |
| WO | WO 01/80656 | 11/2001 |
| WO | WO 02/096408 | 12/2002 |
| WO | WO03086104 A1 | 10/2003 |
| WO | WO 03/105606 | 12/2003 |
| WO | WO 03/106014 | 12/2003 |
| WO | WO 2004/041251 | 5/2004 |

(56) References Cited

FOREIGN PATENT DOCUMENTS

| WO | 2004/054702 | 7/2004 |
|---|---|---|
| WO | WO2007054207 A1 | 5/2007 |
| WO | WO2007055815 A1 | 5/2007 |

OTHER PUBLICATIONS

Reasons for Submission on behalf of Japan Capsular Products Inc. filed in Japanese Patent Application No. 2003-583137 on Nov. 26, 2010.
Bonnet et al., Ullmann's Encyclopedia of Industrial Chemistry, vol. II, p. 668, right col. (2003).
Examination report for Application No. 200780019734.2 dated May 6, 2011.
Examination report for Application No. MX/a/2008/012967 dated Apr. 27, 2011.
Examination report for Application No. 200780029069.5 dated Feb. 24, 2011.
Examination report for Application No. 07825594.0 dated Mar. 30, 2011.
Examination report for Application No. 200880007740.0 dated Mar. 23, 2011.
Examination report for Application No. 2003-583137 dated May 10, 2011.
Limmer, "Remington: The Science and Practice of Pharmacy," p. 332, left col. (2000).
Notice of Allowance for U.S. Appl. No. 11/227,961 dated Jun. 14, 2011.
Response to Opposition for Application No. EP06020381.7 dated Jun. 29, 2011.
Examination Report for Application No. 565606 dated May 13, 2010.
Examination Report for Application No. 573327 dated Nov. 16, 2011.
Examination Report for Application No. 596403 dated Nov. 16, 2011.
Office Action for Application No. 200680032544.X dated Oct. 20, 2011.
Office Action for Application No. 200780019734.2 dated May 6, 2011.
Office Action for Application No. 200780029069.5 dated Feb. 24, 2011.
Office Action for Application No. 200880007740.0 dated Mar. 23, 2011.
Office Action for Application No. 07754635.6 dated Aug. 26, 2011.
Office Action for Application No. 07825594.0 dated Mar. 30, 2011.
Office Action for Application No. 08713076.1 dated Sep. 21, 2011.
Office Action for Application No. 2008-520263 dated Feb. 22, 2011.
Office Action for Application No. 7007996/2005 dated Nov. 4, 2011.
Office Action for Application No. MX/a/2008/000210 dated Oct. 20, 2011.
Office Action for U.S. Appl. No. 11/918,150 dated Nov. 16, 2011.
Office Action for U.S. Appl. No. 12/308,045 dated Sep. 9, 2011.
Office Action for Application No. AU 2007282922 dated Mar. 2, 2012.
Office Action for Application No. AU 2007238985 dated Dec. 5, 2011.
Examination Report for Application No. AU 2008205325 dated Jun. 22, 2012.
Examination Report for Application No. CL 2008-63 dated May 15, 2012.
Office Action for Application No. CN 200780019734.2 dated Apr. 25, 2012.
Office Action for Application No. CN 200780029069.5 dated Apr. 27, 2012.
Office Action for Application No. CN 200880007740.0 dated Mar. 16, 2012.
Office Action for Application No. EP 07825594.0 dated Aug. 31, 2011.
Office Action for Application No. EP 07754635.6 dated Dec. 21, 2009.
Office Action for Application No. EP 07754635.6 dated Mar. 6, 2012.
Office Action for Application No. EP 11196119.9 dated Mar. 1, 2012.
Office Action for Application No. EP 06773967.2 dated May 18, 2012.
Examination Report for Application No. JP 2009-523371 dated Sep. 24, 2012.
Examination Report for Application No. JP 2009-545586 dated Sep. 19, 2012.
Office Action for Application No. JP 2003-583137 dated Jan. 24, 2012.
Examination Report for Application No. JP 2003-583137 dated Aug. 24, 2012.
Office Action for Application No. JP 2009-504244 dated Feb. 20, 2011.
Examination Report for Application No. JP 2010-190957 dated Oct. 16, 2012.
Office Action for Application No. KR 10-2011-7022451 dated Dec. 22, 2011.
Office Action for Application No. MX/a/2008/015556 dated Mar. 15, 2012.
Office Action for Application No. MX/a/2008/000210 dated Feb. 20, 2012.
Office Action for Application No. NZ 573327 dated Dec. 8, 2011.
Office Action for Application No. NZ 578872 dated Nov. 11, 2011.
Office Action for Application No. NZ 572529 dated May 21, 2010.
Response to Office Action for NZ 572529 dated Oct. 1, 2010.
Office Action for Application No. NZ 572529 dated Oct. 22, 2010.
Examination Report for Application No. NZ 600903 dated Jul. 3, 2012.
Office Action for Application No. PE 000110-2008 dated Feb. 29, 2012.
Office Action for U.S. Appl. No. 11/435,605 dated Sep. 2, 2010.
Response to Office Action for U.S. Appl. No. 11/435,605 dated Nov. 5, 2010.
Office Action for U.S. Appl. No. 11/435,605 dated Jan. 24, 2011.
Response to Office Action for U.S. Appl. No. 11/435,605 dated Apr. 13, 2011.
Office Action for U.S. Appl. No. 12/308,045 dated Feb. 17, 2012.
Office Action for U.S. Appl. No. 12/768,152 dated Sep. 12, 2012.
Extended European Search Report for Application No. EP 07825594.0 dated Aug. 31, 2011.
Response to Office Action for U.S. Appl. No. 12/308,045 dated Aug. 7, 2012.
Office Action for U.S. Appl. No. 12/308,045 dated Nov. 16, 2012.
Schrooyen et al., Microencapsulation: its application in nutrition, Proceedings of the Nutrition Society, 60:475-479 (2001).
Summons to Attend Oral Proceedings for Application No. EP 03711759.5 dated Jan. 4, 2012.
Summons to Attend Oral Proceedings for Application No. EP 06020381.7 dated Jan. 4, 2012.
Office Action for U.S. Appl. No. 12/522,826 dated Aug. 7, 2012.
Office Action for U.S. Appl. No. 12/522,826 dated Feb. 28, 2013.
Chourpa, Igor, et al., "Conformational Modifications of α Gliadin and Globulin Proteins upon Complex Coacervates Formation with Gum Arabic as Studied by Raman Microspectroscopy," Biomacromolecules, vol. 7, 2006, pp. 2616-2623.
Jizomoto, Hiroaki, "Phase Separation Induced in Gelatin-Base Coacervation Systems by Addition of Water-Soluble Nonionic Polymers I: Microencapsulation," Journal of Pharmaceutical Sciences, vol. 73, No. 7, 1984, pp. 879-882.
Office Action for U.S. Appl. No. 12/308,045 dated Oct. 7, 2013.
Office Action for U.S. Appl. No. 12/522,826 dated Jul. 2, 2013.
Office Action for U.S. Appl. No. 12/768,152 dated Jul. 25, 2013.
Office Action for Application No. KR 1020097000087 dated Oct. 18, 2013 (English Translation).
Office Action for Application No. EP 08713076.1 dated Feb. 18, 2013.
Appel et al., "Does supplementation of diet with 'fish oil' reduce blood pressure? A meta-analysis of controlled clinical trials," *Arch Intern Med.*, 153(12):1429-1438 (1993).
Barrow et al., "Stabilization of highly unsaturated fatty acids and delivery into foods," *Lipid Technology*, 9(5):108-111 (2007).

(56) References Cited

OTHER PUBLICATIONS

Beestman, "Microencapsulation of Solid Particles," Chemical Abstract, Abstracts of Papers, 220th ACS National Meeting, Washington, DC, United States, Aug. 20-24, 2000, AGRO-037. CODEN: 69FZC3 AN 2000:793223.

Boh et al., "Microcapsule Applications: Patent and Literature Analysis," *MML Series*, 6:85-156 (2003).

Borghi, "Omega-3 LC PUFAs, A new solution for pasteurized milk enrichment," *Wellness Foods Europe*, pp. 25-26 (May 2005).

Calon et al., "Docosahexaenoic acid protects from dentritic pathology in an Alzeheimer's Disease mouse model," *Neuron*, 43:633-645 (2004).

Choi et al., "Physicochemical and sensory characteristics of fish gelatin," *J. Food Sci. Food Chemistry and Toxicology*, 65:194-199 (2000).

Dyerberg et al., "In Omega-3 fatty acids: prevention and treatment of vascular disease," Kristensen et al., Eds. Bi. & Gi Publ., Verona-Springer-Verlag, London, pp. 217226 (1995).

Encyclopedia of Pharmaceutical Technology, "Micoencapsulation," Editors; James Swarbrick and James C. Boylan, Marcel Dekker, Inc., New York, vol. 9, pp. 423-441, 1994.

European Patent Office European Search Report for 06020381.7 dated Apr. 10, 2007.

European Search Authority International Search Report for PCT/IB2006/001214 and Written Opinion mailed Feb. 8, 2007.

Fong, "Microencapsulation by solvent and organic phase separation processes," *Controlled Release Systems: Fabrication Technology*, Hsieh Ed., CRC Press, New York, pp. 99-105 (1988).

GISSI-Prevenzione Investigators, "Dietary supplementation with Omega-3 polyunsaturated fatty acids and vitamin E after myocardial infarction: results of the GISSI-Prevenzione trial," *Lancet*, 354:447-455 (1999).

Goyer, "Toxic effects of metals," *Casarett and Doull's Toxicology*, Amdur et al., Eds., 4th ed., Pergamon Press, New York, pp. 638-639 (1991).

Harris, "Extending the cardiovascular benefits of Omega-3 fatty acids," *Curr. Atheroscler Rep.*, 7:375-380 (2005).

Haug et al., "Physical and rheological properties of fish gelatin compared to mammalian gelatin," *Food Hydrocolloids*, 18:203-213 (2004).

Holub, "Clinical Nutrition: 4 Omega-3 fatty acids in cardiovascular care," *CMAJ*, 166(5):608-615 (2002).

http://en.wikipedia.org/wiki/morula, 2011.

http://www.advancedfertility.com/4cell.htm, 2011.

http://www.advancedfertility.com/8cell.htm, 2011.

http://www.advancedfertility.com/morula.htm, 2011.

Ijichi et al., "Multi-Layered GelatinAcacia Microcapsules by Complex Coacervation Method," *J. of Chem Eng. of Japan.*, 30(5):793-798 (1997).

Kage et al., "Microencapsulation of mono-dispersed droplets by complex coacervation and membrane thickness of generated capsules," Chemical Abstract No. Accession 615273 (2000).

Kas et al., "Microencapsulation using coacervatoin/phrase separation," *In Handbook of Pharmaceutical Controlled Release Technology*, Wise Ed., Marcel Dekker Inc., New York, pp. 301-328 (2000).

Kondo et al., "Microencapsulation utilizing phase separation from an aqueous solution system," *Microcapsule Processing and Technology*, Marcel Dekker Inc., New York, pp. 70-95 (1979).

Kris-Etherton et al., "Fish consumption, fish oil, Omega-3 fatty acids and cardiovascular disease," *The American Heart Association Scientific Statement*, 106(21):2747-2757 (Nov. 2002).

Leclercq et al., "Formation and characterization of microcapsules by complex coacervation with liquid or solid aroma cores," *Flavour Fragr. J.*, 24:17-24 (2009).

Magdassi et al., "Microencapsulation of Oil-in-Water Emulsions by Proteins," *Microencapsulation—Methods and Industrial Applications*, edited by Simon Benita, Marcel Dekker, Inc., New York, pp. 21-33 (1996).

Marcus et al., "The Vitamins," *Goodman and Gilman's the Pharmacological Basis of Therapeutics*, McGraw-Hill, Inc., New York, pp. 1524-1527 (1990).

Mori et al., "Purified eicosapentaenoic and docosapentaenoic acids have differential effects on serum lipids and lipoproteins, LDL particle size, glucose, and insulin in mildly hypelipidemic men," *Am. J. Clin. Nutr.*, 71:1085-1094 (2000).

Muskiet et al., "Is docosahexaenoic acid (DHA) essential? Lessons from DHA status regulation, our ancient diet, epidemiology and randomized controlled trials," *J. Nutr.*, 134(1):183-186 (2004).

O'Keefe et al., "Omega-3 acids: Time for clinical implementation?" *Am. J. Cardiology*, 85:1239-1241 (2002).

Onuki et al., "In vivo effects of highly purified docosahexaenoic acid on rectal insulin absorption," *Int. J Pharm.*, 198:147-156 (2000).

Ovide-Borodeaux et al., "Docosahexaenoic acid affects insulin-deficiency and insul resistant-induced alterations in cardiac mitochondria," *Am. J. Physiool. Regul. Integr. Comp. Physiol.*, 286:R519-R527 (2003).

Radack et al., "The effects of low doses of Omega-3 fatty acid supplementation on blood pressure in hypertensive subjects: a randomized controlled trial," *Arch. Intern. Med.*, 151:1173-1180 (1991).

Recommended Daily Allowances, Ninth Revised Edition, The Natural Academy of Sciences, p. 160 (1980).

Soper, "Utilization of coacervated flavors," *Encapsulation and Controlled Release of Food Ingredients*, Risch and Reineccius Ed., ACS Symposium Series 590, Washington, D.C., pp. 104-112 (1995).

Sparks, "Microencapsulation," *Kirk-Othmer*, Encyclopedia of Chemical Technology, vol. 15, 3rd Ed., John Wiley & Sons Inc., New York, pp. 470-793 (1981).

Sugano et al., "Balanced intake of polyunsaturated fatty acids for health benefits," *J. Oleo. Sci.*, 50(5):305-311 (2001).

Thimma et al., "Study of complex coacervation of gelatin with sodium carboxymethyl guar gum: Microencapsulation of close oil and sulphamethoxazole," *J. Microencapsulation*, 20(2):203-210 (2003).

Webb, "Alternative sources of Omega-3 fatty acids," *Natural Foods Merchandiser*, XXVI(8):40-44 (2005).

Whorton et al., "Evaluation of the mechanisms associated with the release of encapsulated flavor form maltodextrin matrices," *Encapsulation and Controlled Release of Food Ingredients*, Risch and Reineccius Ed., ACS Symposium Series 590, Washington, D.C., pp. 143-160 (1995).

Yoshida et al., "Manufacture of microcapsules from complex coacervation processes," *Chemical Abstract*, Accession No. 140735 (1990).

\* cited by examiner

MICROCAPSULES HAVING MULTIPLE SHELLS AND METHOD FOR THE PREPARATION THEREOF

CROSS-REFERENCE TO RELATED APPLICATIONS

This application is a continuation of U.S. application Ser. No. 12/642,303, filed Dec. 18, 2009, and which is a continuation of U.S. application Ser. No. 10/497,290, filed Nov. 4, 2003, now abandoned, and which claims the benefit of priority to U.S. Provisional Patent Application No. 60/423,363 filed Nov. 4, 2002, which applications are incorporated by reference herein in their entireties.

FIELD OF THE INVENTION

This invention relates to microcapsules having multiple shells, to methods of preparing microcapsules and to their use.

BACKGROUND OF THE INVENTION

Microcapsules are small particles of solids, or droplets of liquids, inside a thin coating of a shell material such as starch, gelatine, lipids, polysaccharides, wax or polyacrylic acids. They are used, for example, to prepare liquids as free-flowing powders or compressed solids, to separate reactive materials, to reduce toxicity, to protect against oxidation and/or to control the rate of release of a substance such as an enzyme, flavour, a nutrient, a drug, etc.

Ideally, a microcapsule would have good mechanical strength (e.g. resistance to rupture) and the microcapsule shell would provide a good barrier to oxidation, etc.

A typical approach to meeting these requirements is to increase the thickness of the microcapsule wall. But this results in an undesirable reduction in the loading capacity of the microcapsule. That is, the "payload" of the microcapsule, being the mass of the loading substance encapsulated in the microcapsule divided by the total mass of the microcapsule, is low. The typical payload of such "single-core" microcapsules made by spray drying an emulsion is in the range of about 25-50%.

Another approach to the problem has been to create what are known as "multi-core" microcapsules. These microcapsules are usually formed by spray drying an emulsion of core material such that the shell material coats individual particles of core material, which then aggregate and form a cluster. A typical multi-core microcapsule is depicted in prior art FIG. 1. Multi-core microcapsule 10 contains a plurality of cores 12. The cores 12 take the form of entrapped particles of solids or of liquid droplets dispersed throughout a relatively continuous matrix of shell material 14. As a result, there is a high ratio of shell material to loading material and the payload of the multi-core microcapsule is therefore low. Moreover, despite the high ratio of shell material to loading substance in such microcapsules, the shell material is poorly distributed. As shown in prior art FIG. 1, many of the cores 12 are very close to the surface 16 of the microcapsule. The cores at the surface are therefore not well protected against rupture or from oxidation.

Known microcapsules therefore either have a poor payload, or fail to adequately contain and protect the loading substance deposited therein. Moreover, because these microcapsules are generally prepared in a single step, it is difficult to incorporate multiple functionalities, such as oxidation resistance, moisture resistance and taste masking into a single microcapsule.

SUMMARY OF THE INVENTION

In one aspect, the invention provides a multi-core microcapsule comprising: (a) an agglomeration of primary microcapsules, each primary microcapsule comprising a core and a first shell surrounding the core; (b) a second shell surrounding the agglomeration; and (c) a third shell surrounding the second shell; at least one of the first, second and third shells comprising a complex coacervate.

In another aspect, the invention provides a single-core microcapsule comprising: (a) a core; (b) a first shell surrounding the core; and (c) a second shell surrounding the first shell; at least one of the first and second shells comprising a complex coacervate.

In the case of either the multi-core or single-core microcapsules, it is preferred that all of the shells comprise a complex coacervate, which may be the same or different for each of the shells. Additional shells, e.g. from 1 to 20, may be added to further strengthen the microcapsule.

In another aspect, the invention provides a process for making a microcapsule having a plurality of shells, the process comprising:
(a) providing a microcapsule selected from the group consisting of:
  (i) a multi-core microcapsule comprising: an agglomeration of primary microcapsules, each primary microcapsule comprising a core and a first shell surrounding the core; and a second shell surrounding said agglomeration; and
  (ii) a single-core microcapsule comprising: a core; and a first shell surrounding the core;
(b) mixing the microcapsule with first and second polymer components of shell material in aqueous solution;
(c) adjusting at least one of pH, temperature, concentration and mixing speed to form shell material comprising the first and second polymer components, the shell material forming an additional shell enveloping the microcapsule;
wherein at least one of the first shell, the second shell and the additional shell comprises a complex coacervate.

DETAILED DESCRIPTION OF THE PREFERRED EMBODIMENTS

Core Materials

Figure 1:
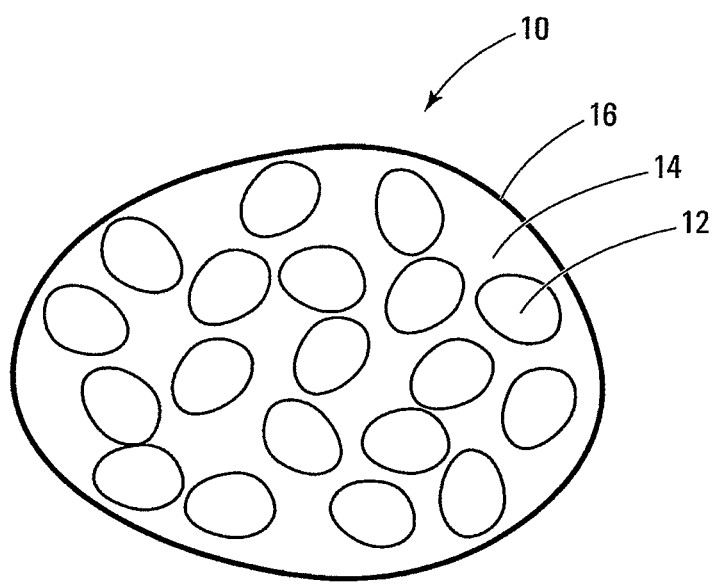
FIG. 1 depicts a typical prior art multi-core microcapsule.

Any core material that may be encapsulated in microcapsules is useful in the invention. Indeed, in certain embodiments, commercially available microcapsules may be obtained and then further processed according to the processes of the invention.

When the initial multi-core microcapsules are prepared according to processes as described herein involving an aqueous solution, the core material may be virtually any substance that is not entirely soluble in the aqueous solution. Preferably, the core is a solid, a hydrophobic liquid, or a mixture of a solid and a hydrophobic liquid. The core is more preferably a hydrophobic liquid, such as grease, oil or a mixture thereof. Typical oils may be fish oils, vegetable oils, mineral oils, derivatives thereof or mixtures thereof. The loading substance may comprise a purified or partially purified oily substance such as a fatty acid, a triglyceride or a mixture thereof. Omega-3 fatty acids, such as $\alpha$-linolenic acid (18:3n3), octadecatetraenoic acid (18:4n3), eicosapentaenoic acid (20:5n3) (EPA) and docosahexaenoic acid (22:6n3) (DHA), and derivatives thereof and mixtures thereof, are preferred. Many types of derivatives are well known to one skilled in the art. Examples of suitable derivatives are esters, such as phytosterol esters, branched or unbranched $C_1$-$C_{30}$ alkyl esters, branched or unbranched $C_2$-$C_{30}$ alkenyl esters or branched or unbranched $C_3$-$C_{30}$ cycloalkyl esters, in particular phytosterol esters and $C_1$-$C_6$ alkyl esters. Preferred sources of oils are oils derived from aquatic organisms (e.g. anchovies, capelin, Atlantic cod, Atlantic herring, Atlantic mackerel, Atlantic menhaden, salmonids, sardines, shark, tuna, etc) and plants (e.g. flax, vegetables, algae, etc).

While the core may or may not be a biologically active substance such as a tocopherol, antioxidant or vitamin, the microcapsules of the present invention are particularly suited for biologically active substances, for example, drugs, nutritional supplements, flavours, antioxidants or mixtures thereof.

Shell Material

Coacervation is a phase separation phenomenon, in which a homogenous polymer solution is converted into two phases. One is a polymer-rich phase, called a coacervate. The other is a polymer-poor phase, i.e., solvent. Complex coacervation is caused by the interaction of two oppositely charged polymers.

Preferably, a positively charged polymer component "A" interacts with a negatively charged polymer component "B". For example, positively charged type A gelatine ("component A") forms complex coacervates with negatively charged polyphosphate ("component B"). Other systems that have been studied are gelatine/gum Acacia, gelatine/pectin, gelatine/carboxymethyl guar gum and whey protein/gum arabic.

Component A is preferably gelatine type A, chitosan, etc., although other polymers are also contemplated as component A. Component B is preferably gelatine type B, polyphosphate, gum arabic, alginate, carrageenan, pectin, carboxymethylcellulose, or a mixture thereof.

In addition to the charge density of the two polymer components, complex coacervation depends on other factors such as molecular weight of the polymers and their ratio, ionic strength, pH and temperature of the medium (*J. Microencapsulation*, 2003, Vol. 20, No. 2: 203-210).

The molar ratio of component A:component B that is used depends on the type of components but is typically from 1:5 to 15:1. For example, when gelatine type A and polyphosphate are used as components A and B respectively, the molar ratio of component A:component B is preferably 8:1 to 12:1; when gelatine type A and gelatine type B are used as components A and B respectively, the molar ratio of component A:component B is preferably 2:1 to 1:2; and when gelatine type A and alginate are used as components A and B respectively, the molar ratio of component A:component B is preferably 3:1 to 5:1.

One suitable process of microencapsulation using complex coacervation comprises three steps: 1) dispersing the loading substance into a system of at least one of the polymers for the complex coacervate; 2) forming shells by deposition of coacervates which derive from the polymeric components under controlled conditions of temperature, pH, concentration of colloids, mixing speed etc.; and 3) hardening of the shells by crosslinking of the coacervates deposited on microcapsules (*Ullmann's Encyclopedia of Industrial Chemistry* 6th edition. 2001, Vol. A16. pp. 575-588).

Any shells that do not comprise complex coacervates may be formed of any material that can form an additional shell around the microcapsule. The additional shell material typically comprises at least one polymer component. Examples of polymer components include, but are not limited to, proteins, e.g. gelatines, soy proteins, whey proteins, and milk proteins, polyphosphate, polysaccharides and mixtures thereof. Preferred polymer components are gelatine A, gelatine B, polyphosphate, gum arabic, alginate, chitosan, carrageenan, pectin, cellulose or derivatives of cellulose such as carboxymethylcellulose (CMC) or a mixture thereof. A particularly preferred form of gelatine type A has a Bloom strength of 50-350, more preferably a Bloom strength of about 275.

The shell material can also comprise lipids, such as waxes, fatty acids and oils, etc. to provide desired functionalities. The incorporation of lipids into the shell material improves the impermeability of the shell to water and oxygen. A preferred lipid for this purpose is beeswax. These lipids may be in solid, semi-solid or liquid form.

Processing Aids

Processing aids may be included in the shell material. Processing aids may be used for a variety of reasons. For example, they may be used to promote agglomeration of primary microcapsules when forming multi-core microcapsules, control microcapsule size and shape and/or to act as an antioxidant. Antioxidant properties are useful both during the process (e.g. during coacervation and/or spray drying) and in the microcapsules after they are formed (e.g. to extend shelf-life of loading substances which are readily oxidized, etc). Preferably a small number of processing aids that perform a large number of functions are used. For example, ascorbic acid or a salt thereof may be used to promote agglomeration of the primary microcapsules, to control microcapsule size and shape and to act as an antioxidant. The ascorbic acid or salt thereof is preferably used in an amount of about 100 ppm to about 10,000 ppm, more preferably about 1000 ppm to about 5000 ppm relative to the batch size (i.e., the total weight). A salt of ascorbic acid, such as sodium or potassium ascorbate, is particularly preferred in this capacity. Other processing aids include, without limitation, buffering acids and/or their salts such as phosphoric acid, acetic acid, citric acid, and the like.

Structure of Microcapsules

Figure 2:
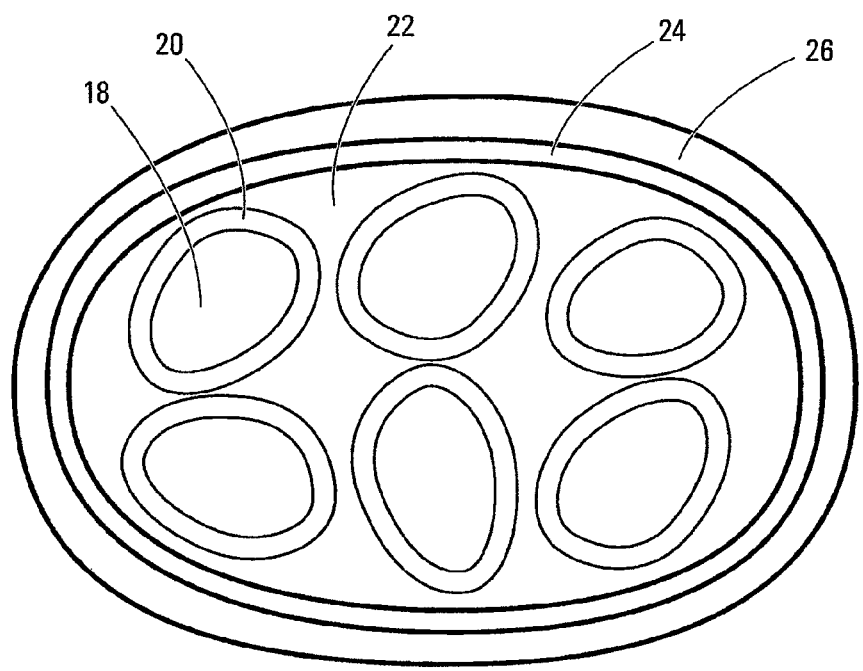
FIGS. 2 and 3 depict embodiments of the invention in which multi-core microcapsules are provided having multiple shells.

In one embodiment, microcapsules of the invention have a structure generally as depicted in FIG. 2. FIG. 2 depicts a multi-core microcapsule prepared according to a multi-step process of the invention. Primary microcapsules comprise cores 18 (i.e. the loading substance) surrounded by first shells 20. The primary microcapsules agglomerate and the space 22 between them is usually at least partly filled by additional shell material of same composition as first shell 20, although there may be voids between some of the primary microcapsules. The agglomeration of primary microcapsules is surrounded by a second shell 24.

Multi-core microcapsules comprising second shell 24 may be prepared according to the processes described herein and exemplified in the examples or by generally the same techniques that are described in Applicant's co-pending U.S. patent application Ser. No. 10/120,621 filed Apr. 11, 2002, corresponding to International Application No. PCT/CA2003/000520 filed Apr. 8, 2003, the disclosures of both of which are incorporated herein by reference. These multi-core microcapsules are particularly useful because the foam-like structure of primary microcapsules, supported by additional shell material in space 22 and surrounded by second shell 24 is an extremely strong, rupture-resistant structure that has a high payload i.e. the ratio of the total mass of the cores to the total mass of the multi-core microcapsule is very high, e.g. at least 50, 55, 60, 65, 70, 75, 80, 85, 90% or higher. This is called a "one-step" process when shells 20 and 24 are of the same composition and formed in a single step. When shells 20 and 24 are of different composition, the process involves two steps.

Commercially available multicore microcapsules may also be used as starting materials. An example is the Driphorm™ Hi-DHA™ microencapsulated tuna oil, manufactured by Nu-Mega Ingredients Pty. Ltd., Queensland, AU.

In accordance with the invention, a three-step process takes place when a third shell 26 is formed on the multi-core microcapsule. Third shell 26 further strengthens the microcapsule and can be advantageously used to provide a shell having properties different from those of shell 24. For instance, different polymer components can be incorporated into third shell 26. In addition, or alternatively, lipids may be incorporated into shell 26 to increase moisture or oxygen impermeability or the like. These properties might instead be incorporated into second shell 24 rather than third shell 26 (or also into second shell 24 as well as into third shell 26), depending on the requirements for a particular purpose. Additional shells, not shown in FIG. 2, may be formed around third shell 26, by the methods and techniques of the invention. For instance, N additional shells could be added, wherein N is an integer from 1 to 20.

At least one of shells 20, 24 and 26 and of any additional shells comprises a complex coacervate, as described above. Preferably, at least two of the shells comprise a complex coacervate. Even more preferably, all of the shells comprise a complex coacervate. For instance, the following shells may comprise complex coacervates: (a) shell 20; (b) shell 24; (c) shell 26; (d) shells 20 and 24; (e) shells 20 and 26; (f) shells 24 and 26; or (g) shells 20, 24 and 26. Additional shells also preferably comprise a complex coacervate.

Referring again to FIG. 2, the primary microcapsules (i.e. cores 18 surrounded by first shells 20) typically have an average diameter of about 40 nm to about 10 µm, more particularly from about 0.1 µm to about 5 µm, even more particularly an average diameter of about 1-2 µm. The finished multi-core microcapsule, i.e. including third shell 26, usually has an average diameter from about 1 µm to about 2000 µm, more typically from about 20 µm to about 1000 µm, more particularly from about 20 µm to about 100 µm and even more particularly from about 50 µm to about 100 µm.

Figure 3:
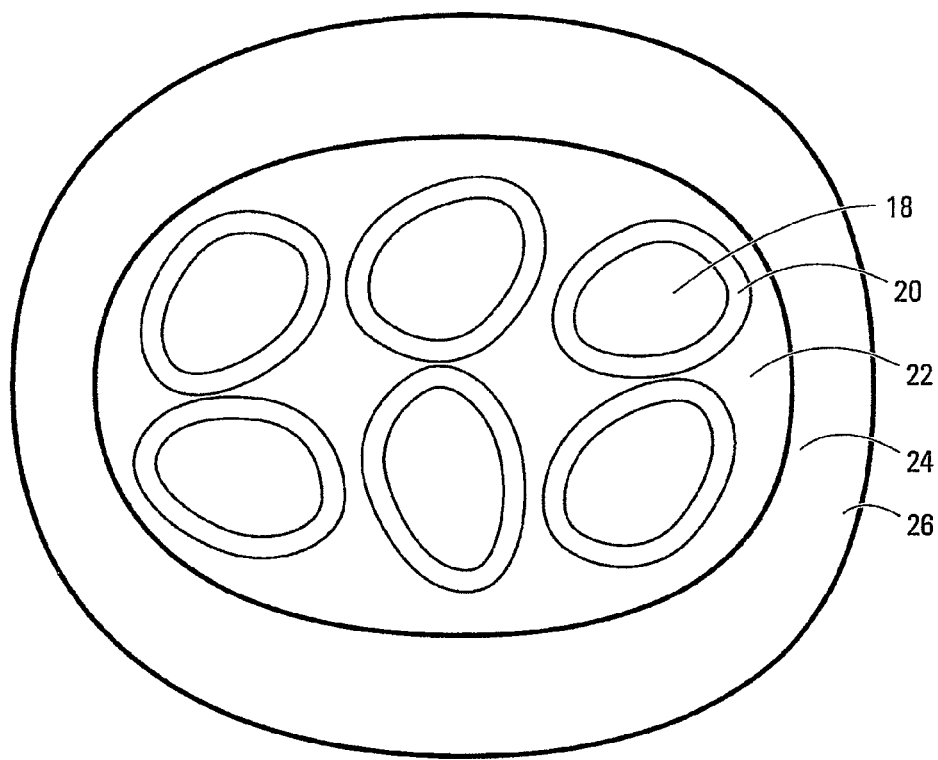

In FIG. 2, second shell 24 and third shell 26 are depicted as discrete layers. This will be the case if the shells are formed of the different shell materials. In that case, even if they do not differ in appearance, they will have a different composition and can be represented as discrete, distinct layers. But if second shell 24 and third shell 26 are formed of the same shell material, they may, as shown in FIG. 3, merge to form a single, continuous layer, having the combined thickness of second shell 24 and third shell 26. As shown in FIG. 3, when the second and third shells are of the same composition, there may be no discrete boundary separating them. This would be true also in microcapsules of the invention having fourth or additional shells that are of the same composition as the preceding shell.

Figure 4:
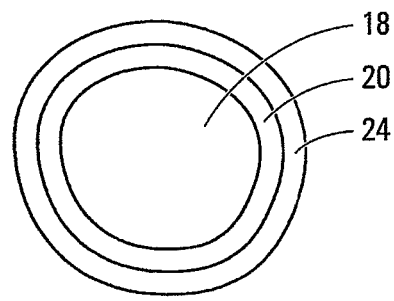
FIGS. 4 and 5 depict embodiments of the invention in which single-core microcapsules are provided having multiple shells.

The invention is also useful in the preparation of single-core microcapsules having multiple shells. Single-core microcapsules useful as starting materials are commercially available. Examples include microencapsulated flavours by Givaudan Flavors Corp., Cincinnati, Ohio, USA, and microencapsulated minerals and vitamins by Watson Food Co. Inc., West Haven, Conn., USA. Alternatively, they can be made by complex coacervation processes as described herein, e.g. by preparing primary microcapsules without a further agglomeration step. FIG. 4 depicts a single-core microcapsule having multiple shells in accordance with the invention. Core 18 is surrounded by a first shell 20 and a second shell 24. Additional shells, not shown in FIG. 4, may be formed around second shell 24, by the methods and techniques of the invention. For instance, N additional shells could be added, wherein N is an integer from 1 to 20.

As with the multi-core microcapsules, shells 20 and 24 of single-core microcapsules may be of the same or different composition. At least one of shells 20 and 24 and of any additional shells comprises complex coacervates as described above. Preferably, at least two of the shells comprise a complex coacervate. Even more preferably all of the shells comprise a complex coacervate. For instance, the following shells may comprise complex coacervates: (a) shell 20; (b) shell 24; or (c) shells 20 and 24. Additional shells also preferably comprise complex coacervates.

Single-core microcapsules may be as large as multi-core microcapsules. For instance, the exterior diameter of second shell 24 in the single-core microcapsule of FIG. 4 may be from about 1 µm to about 2000 µm. More typically it will be from about 20 µm to about 1000 µm, more particularly from about 20 µm to about 100 µm and even more particularly from about 50 µm to about 100 µm.

Figure 5:
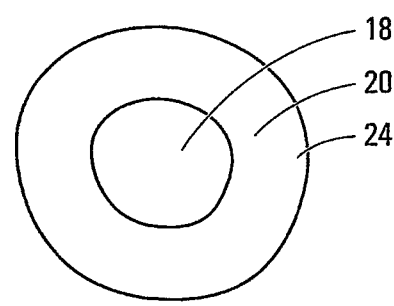

When they are of the same composition, first shell 20 and second shell 24 (and any additional shell) of the single-core multicapsule may merge to form a single continuous layer as depicted in FIG. 5. This may be done in a one-step process.

Processes

Single or multi-core microcapsules to which additional shells may be added by the processes of the invention may be obtained from commercial sources. In a particularly preferred embodiment, multi-core microcapsules prepared in accordance with applicant's co-pending U.S. patent application Ser. No. 10/120,621 filed Apr. 11, 2002, corresponding to International Application No. PCT/CA2003/000520 filed Apr. 8, 2003, the disclosures of both of which are incorporated herein by reference, are used. Such microcapsules can be prepared e.g. by a one step process as follows.

An aqueous mixture of a loading substance (i.e. core material) and a polymer component of the shell material is formed.

The aqueous mixture may be a mechanical mixture, a suspension or an emulsion. When a liquid loading material is used, particularly a hydrophobic liquid, the aqueous mixture is preferably an emulsion of the loading material and the polymer components.

In a more preferred aspect, a first polymer component is provided in aqueous solution, preferably together with processing aids, such as antioxidants. A loading substance may then be dispersed into the aqueous mixture, for example, by using a homogenizer. If the loading substance is a hydrophobic liquid, an emulsion is formed in which a fraction of the first polymer component begins to deposit around individual droplets of loading substance to begin the formation of primary shells. If the loading substance is a solid particle, a suspension is formed in which a fraction of the first polymer component begins to deposit around individual particles to begin the formation of primary shells. At this point, another aqueous solution of a second polymer component may be added to the aqueous mixture.

Droplets or particles of the loading substance in the aqueous mixture preferably have an average diameter of less than 100 µm, more preferably less than 50 µm, even more preferably less than 25 µm. Droplets or particles of the loading substance having an average diameter less than 10 µm or less than 5 µm or less than 3 µm or less than 1 µm may be used. Particle size may be measured using any typical equipment known in the art, for example, a Coulter™ LS230 Particle Size Analyzer, Miami, Fla., USA.

The amount of the polymer components of the shell material provided in the aqueous mixture is typically sufficient to form both the primary and outer shells of microcapsules. Preferably, the loading substance is provided in an amount of from about 1% to about 15% by weight of the aqueous mixture, more preferably from about 3% to about 8% by weight, and even more preferably about 6% by weight.

If a complex coacervate is desired, the pH, temperature, concentration, mixing speed or a combination thereof is then adjusted to accelerate the formation of the primary shells of complex coacervate around the droplets or particles of the loading substance to form primary microcapsules. In the case of multicore microcapsules, agglomeration of the primary microcapsules will take place to form discrete clumps at desired size and shape.

pH is an expression of the concentration of hydrogen ions in solution. Such ions affect the ionization equilibria of the component A and B polymers involved in complex coacervation and thus the formation of complex coacervates. The pH is adjusted so that the component A polymer will bear a net positive charge and the component B polymer will bear a net negative charge. Hence, the pH adjustment depends on the type of shell material to be used.

For example, when gelatine type A is a polymer component, the gelatine molecules have nearly equal positive and negative charges (i.e. zero net polarity change) at their point of zero charge (pzc) around pH 9-10. Only when the solution pH is lower than the pzc value, will the polymer bear a net positive charge, which interacts with the negatively charged component B (e.g. gum arabic, polyphosphate, alginate, etc.).

In the case of gelatine type A, the pH is preferably adjusted to a value from 3.5-5.0, more preferably from 4.0-5.0. Much outside this range, the gelatine-based complex tends to form gels upon cooling rather than a shell on the microcapsules. If the pH of the mixture starts in the desired range, then little or no pH adjustment is required.

The molar ratio of components A and B is adjusted to favour formation of shells on the microcapsules rather than merely the formation of gel particles in solution. Suitable molar ratios are discussed above under the heading "Shell Material".

The concentration of components A and B in the aqueous mixture may also affect the formation of complex coacervates and can be adjusted accordingly. Typically, the total concentration of components A and B varies from 1% to 20%, preferably 2-10%, and more preferably 3-6% by weight of the aqueous mixture. For instance, when gelatine type A is used as component A, the concentration of gelatine type A is preferably from 1-15% by weight of the aqueous mixture, more preferably 2-6% by weight and even more preferably 2-4% by weight. Similarly, when polyphosphate is used as component B, its concentration in the aqueous mixture is preferably 0.01-0.65% by weight of the aqueous mixture, more preferably 0.13-0.17% by weight, even more preferably 0.13-0.26% by weight.

The initial temperature of the aqueous mixture is preferably set to a value of from about 40° C. to about 60° C., more preferably at about 50° C.

Mixing speed influences the deposition of complex coacervates on the surface of microcapsules. If the mixing speed is too low, the aqueous mixture is agitated insufficiently and undesirably large microcapsules may be formed. Conversely, if the mixing speed is too high, high shear forces are generated and prevent shell material from forming on the microcapsules. Instead, gel particles form in the solution. The mixing speed is preferably between 100 and 1500 rpm, more preferably between 400 and 1000 rpm and even more preferably between 600 and 800 rpm. Particular mixing parameters depend on the type of equipment being used. Any of a variety of types of mixing equipment known in the art may be used. Particularly useful is an axial flow impeller, such as Lightnin™ A310 or A510.

At this time, materials for outer shell are added into the mixture, and the aqueous mixture may then be cooled under controlled cooling rate and mixing parameters to permit coating of the primary microcapsules to form outer shells. It is advantageous to control the formation of the outer shell at a temperature above the gel point of the shell material. It is also possible at this stage to further add more polymer components, either of the same kind or a different kind, in order to thicken the outer shell and/or produce microcapsules having different layers of shells to provide desired functionalities. The temperature is preferably lowered at a rate of about 1° C./10 minutes until it reaches a temperature of from about 5° C. to about 10° C., preferably about 5° C. The outer shell encapsulates the primary microcapsules or clumps to form a rigid encapsulated agglomeration of microcapsules.

At this stage, a cross-linker may be added to further increase the rigidity of the microcapsules by cross-linking the shell material in both the outer and primary shells and to make the shells insoluble in both aqueous and non-aqueous (e.g., oil) media. Any suitable cross-linker may be used and the choice of cross-linker depends somewhat on the choice of shell material. Preferred cross-linkers are enzymatic cross-linkers (e.g. transglutaminase), aldehydes (e.g. formaldehyde or gluteraldehyde), tannic acid, alum, organic or inorganic calcium or potassium salt, or a mixture thereof. When the microcapsules are to be used to deliver a biologically active substance to an organism, the cross-linkers are preferably non-toxic or of sufficiently low toxicity. The type and the amount of cross-linker used depend on the type of shell material and may be adjusted to provide more or less structural rigidity as desired. For example, when gelatine type A is used in the shell material, transglutaminase may be conveniently used in an amount of about 0.2% to about 2.0%, preferably about 1.0%, by weight of microcapsule suspension. In general, one skilled in the art may routinely determine the desired amount in any given case by simple experimentation.

At this stage, multi-core microcapsules have been produced. These microcapsules or other microcapsules may then be processed in accordance with the invention to add additional shell layers as described above. Preferably, additional shells are added after the formation of the outer shell of the microcapsule or before the cross-linking step. More particularly, first and second polymer components of shell material are dissolved in aqueous solution e.g. at 40 to 60° C., more preferably around 50° C. pH may be controlled or adjusted at this stage. The microcapsules previously prepared are then combined with this mixture. Alternatively, the microcapsules may be combined with an aqueous solution of the first polymer component of shell material and then a second aqueous solution of the second polymer component of shell material may be added. pH, temperature, concentration, mixing speed or a combination thereof can then be adjusted as described above so that the polymer components of shell material form a complex coacervate surrounding and coating the microcapsules with an additional shell. As discussed above, processing aids may be incorporated as may be hydrophobic materials such as oils, waxes, resins or fats. The new outer shell may be then cross-linked as described above. These additional steps of forming additional shell layers may be repeated as desired to build up a suitable number of further shells on the microcapsule.

Finally, the microcapsules may be washed with water and/or dried to provide a free-flowing powder. Drying may be accomplished by a number of methods known in the art, such as freeze drying, drying with ethanol or spray drying. Spray drying is a particularly preferred method for drying the microcapsules. Spray drying techniques are disclosed in "Spray Drying Handbook", K. Masters, 5$^{th}$ edition, Longman Scientific Technical UK, 1991, the disclosure of which is hereby incorporated by reference.

Uses

The microcapsules produced by the processes of the present invention may be used to prepare liquids as free-flowing powders or compressed solids, to store a substance, to separate reactive substances, to reduce toxicity of a substance, to protect a substance against oxidation, to deliver a substance to a specified environment and/or to control the rate of release of a substance. In particular, the microcapsules may be used to deliver a biologically active substance to an organism for nutritional or medical purposes. The biologically active substance may be, for example, a nutritional supplement, a flavour, a drug and/or an enzyme. The organism is preferably a mammal, more preferably a human. Microcapsules containing the biologically active substance may be included, for example, in foods or beverages or in drug delivery systems. Use of the microcapsules of the present invention for formulating a nutritional supplement into human food is particularly preferred.

Microcapsules of the present invention have good rupture strength to help reduce or prevent breaking of the microcapsules during incorporation into food or other formulations. Furthermore, the microcapsules' shells can be formulated to be insoluble in both aqueous and non-aqueous (e.g., oil) media, and help reduce or prevent oxidation and/or deterioration of the loading substance during preparation of the microcapsules, during long-term storage, and/or during incorporation of the microcapsules into a formulation vehicle, for example, into foods, beverages, nutraceutical formulations or pharmaceutical formulations.

The invention will now be further illustrated by the following non-limiting examples.

EXAMPLES

Example 1

Multicore Microcapsules Prepared by One-Step Process for Comparison (Both First and Second Shells Having the Same Composition of Gelatine and Polyphosphate)

54.5 grams gelatine 275 Bloom type A (isoelectric point of about 9) was mixed with 600 grams of deionized water containing 0.5% sodium ascorbate under agitation at 50° C. until completely dissolved. 5.45 grams of sodium polyphosphate was dissolved in 104 grams of deionized water containing 0.5% sodium ascorbate. 90 grams of a fish oil concentrate containing 30% eicosapentaenoic acid ethyl ester (EPA) and 20% docosahexaenoic acid ethyl ester (DHA) (available from Ocean Nutrition Canada Ltd.) was dispersed with 1.0% of an antioxidant (mixed natural tocopherols) into the gelatine solution with a high speed Polytron™ homogenizer at 5,500 rpm for 6 minutes. An oil-in-water emulsion was formed. The oil droplet size had a narrow distribution with an average size of about 1 µm measured by Coulter™ LS230 Particle Size Analyzer. The emulsion was diluted with 700 grams of deionized water containing 0.5% sodium ascorbate at 50° C. The sodium polyphosphate solution was then added into the emulsion and mixed with a Lightnin™ agitator at 600 rpm. The pH was then adjusted to 4.5 with a 10% aqueous acetic acid solution. During pH adjustment and the cooling step that followed pH adjustment, a coacervate formed from the gelatine and polyphosphate coated onto the oil droplets to form primary microcapsules. Cooling was carried out to above the gel point of the gelatine and polyphosphate and the primary microcapsules started to agglomerate to form lumps under agitation. Upon further cooling of the mixture, polymer remaining in the aqueous phase further coated the lumps of primary microcapsules to form an encapsulated agglomeration of microcapsules having an outer shell and having an average size of 50 µm. Once the temperature had been cooled to 5° C., 2.7 grams of 50% gluteraldehyde was added into the mixture to further strengthen the shell. The mixture was then warmed to room temperature and kept stirring for 12 hours. Finally, the microcapsule suspension was washed with water. The washed suspension was then spray dried to obtain a free-flowing powder. A payload of 62% was obtained.

Example 2

A Two-Step Process with Gelatine and Polyphosphate in Both First and Second Shells, But Having Different Compositions Step A: 15.6 grams gelatine 275 Bloom type A (isoelectric point of about 9) was mixed with 172 grams of deionized water containing 0.5% sodium ascorbate under agitation at 50° C. until completely dissolved. 1.56 grams of sodium polyphosphate was dissolved in 29.7 grams of deionized water containing 0.5% sodium ascorbate. 69 grams of a fish oil concentrate containing 30% eicosapentaenoic acid ethyl ester (EPA) and 20% docosahexaenoic acid ethyl ester (DHA) (available from Ocean Nutrition Canada Ltd.) was dispersed with 1.0% of an antioxidant (mixed natural tocopherols) into the gelatine solution with a high speed Polytron™ homogenizer at 6,100 rpm for 4 minutes. An oil-inwater emulsion was formed. The oil droplet size had a narrow distribution with an average size of about 1 μm measured by Coulter™ LS230 Particle Size Analyzer. The emulsion was diluted with 319 grams of deionized water containing 0.5% sodium ascorbate at 50° C. The sodium polyphosphate solution was then added into the emulsion and mixed with a Lightnin™ agitator at 600 rpm. The pH was then adjusted to 4.5 with a 10% aqueous phosphoric acid solution. During pH adjustment and the cooling step that followed pH adjustment, a coacervate formed from the gelatine and polyphosphate coated onto the oil droplets to form primary microcapsules, and then the primary microcapsules started to agglomerate to form lumps under agitation. A payload of 80% was obtained at this step.

Step B: A gelatine solution was prepared by dissolving 41.8 grams of gelatine 275 Bloom type A (isoelectric point of about 9) in 460 grams of deionized water containing 0.5% sodium ascorbate under agitation at 50° C. until completely dissolved. A sodium polyphosphate solution was prepared by dissolving 4.18 grams of sodium polyphosphate in 79.5 grams of deionized water containing 0.5% sodium ascorbate. The gelatine and polyphosphate solutions were combined to form a mixture, and pH of the mixture was adjusted to 4.7 with 10% aqueous phosphoric acid.

Step C: The mixture from Step B was added to the mixture with lumps formed in step A. Cooling was carried out under agitation to cause the gelatine and polyphosphate to form coacervates and to coat the lumps formed in Step A to form an outer shell. The microcapsules thus formed had an average size of 60 μm. Once the temperature had been cooled to 5° C., 2.1 grams of 50% gluteraldehyde was added into the mixture to further strengthen the shell. The mixture was then warmed to room temperature and stirred continuously for 12 hours. Finally, the microcapsule suspension was washed with water. The washed suspension was then spray dried to obtain a free-flowing powder. A payload of 59% was obtained.

Example 3

A Two-Step Process having Gelatine and Alginate in the Second Shell

Step A: Same as Step A in Example 2.

Step B: A gelatine solution was prepared by dissolving 23.0 grams of gelatine 275 Bloom type A (isoelectric point of about 9) in 371 grams of deionized water under agitation at 50° C. until completely dissolved. A sodium alginate (ISP Alginates) solution was prepared by dissolving 3.00 grams of sodium alginate in 503.8 grams of deionized water. The gelatine and sodium alginate solutions were combined to form a mixture. The pH of the mixture was adjusted to 5.00 with 10% aqueous phosphoric acid.

Step C: The mixture from Step B was added to the mixture with lumps formed in step A. Cooling was carried out under agitation to cause gelatine and alginate to form coacervates and coat the lumps formed in Step A to form an outer shell. The microcapsules thus formed had an average size of around 80 μm. Once the temperature had been cooled to 5° C., 2.1 grams of 50% gluteraldehyde was added into the mixture to further strengthen the shell. The mixture was then warmed to room temperature and stirred continuously for 12 hours. Finally, the microcapsule suspension was washed with water. The washed suspension was then spray dried to obtain a free-flowing powder. A payload of 53% was obtained.

Example 4

A Three-Step Process to Incorporate Wax and Alginate in the Second Shell and Alginate in the Third Shell Step A: 20.0 grams gelatine 275 Bloom type A (isoelectric point of about 9) was mixed with 220.1 grams of deionized water containing 0.5% sodium ascorbate under agitation at 50° C. until completely dissolved. 2.00 grams of sodium polyphosphate was dissolved in 38.0 grams of deionized water. 88.0 grams of a fish oil concentrate containing 30% eicosapentaenoic acid ethyl ester (EPA) and 20% docosahexaenoic acid ethyl ester (DHA) (available from Ocean Nutrition Canada Ltd.) was dispersed with 1.0% of an antioxidant (mixed natural tocopherols) into the gelatine solution with a high speed Polytron™ homogenizer at 6,100 rpm for 4 minutes. An oil-in-water emulsion was formed. The oil droplet size had a narrow distribution with an average size of about 1 μm measured by Coulter™ LS230 Particle Size Analyzer. The emulsion was diluted with 408.6 grams of deionized water at 50° C. The sodium polyphosphate solution was then added into the emulsion and mixed with a Lightnin™ agitator at 600 rpm. The pH was then adjusted to 4.5 with a 10% aqueous phosphoric acid solution. During pH adjustment and the cooling step that followed pH adjustment, a coacervate formed from the gelatine and polyphosphate coated onto the oil droplets to form primary microcapsules, and then the primary microcapsules started to agglomerate to form lumps under agitation. A payload of 80% was obtained at this step.

Step B: A gelatine solution was prepared by dissolving 8.6 grams of gelatine 275 Bloom type A (isoelectric point of about 9) in 94.5 grams of deionized water under agitation at 65° C. until completely dissolved. 25.8 grams of beeswax melted at 65° C. was emulsified in the gelatine solution with a high speed Polytron™ homogenizer at 6,100 rpm for 4 minutes. A wax-in-water emulsion was formed. An alginate solution was prepared by dissolving 2.3 grams of sodium alginate in 192 grams of deionized water was added to the emulsion, and pH of the mixture was adjusted to 4.7 with 10% aqueous phosphoric acid. The mixture was then added into lump mixtures in step A under agitation at 800 rpm, and cooling was carried out to cause the gelatine-alginate-wax composite material to form a coating onto the lumps formed in Step A to form microcapsules. A payload of 60% was obtained at this step.

Step C: A solution was prepared by dissolving 23.1 grams of gelatine and 2.3 grams of sodium alginate in 384.9 grams of deionized water under agitation at 50° C. until completely dissolved. pH of the mixture was adjusted to 4.5 with 10% aqueous phosphoric acid, and the mixture was then added into microcapsule mixtures formed in step B under agitation at 800 rpm. Cooling was carried out to cause the gelatine-alginate material to form a coating onto the microcapsules that formed in Step B. Once the temperature had been cooled to 5° C., 1.5 grams of transglutaminase was added into the mixture to cross-link the shell. The mixture was then warmed to room temperature and kept stirring for 12 hours. Finally, the microcapsule suspension was spray dried to obtain a free-flowing powder. A final payload of 52% was obtained.

Example 5

A Two-Step Process of Multicore Microcapsules Having Wax and Alginate in the Second Shell Step A: 13.0 grams of gelatine 275 Bloom type A (isoelectric point of about 9) was mixed with 143.0 grams of deionized water containing 0.5% sodium ascorbate under agitation at 50° C. until completely dissolved. 1.3 grams of sodium polyphosphate was dissolved in 24.7 grams of deionized water. 57.2 grams of fish oil containing 18% eicosapentaenoic acid (EPA) and 12% docosahexaenoic acid (DHA) (available from Ocean Nutrition Canada Ltd.) was dispersed with 1.0% of an antioxidant (mixed natural tocopherols) into the gelatine solution with a high speed Polytron™ homogenizer at 8,000 rpm for 4 minutes. An oil-in-water emulsion was formed. The oil droplet size had a narrow distribution with an average size of about 1 μm measured by Coulter™ LS230 Particle Size Analyzer. The emulsion was diluted with 266.0 grams of deionized water at 50° C. The sodium polyphosphate solution was then added into the emulsion and mixed with a Lightnin™ agitator at 350 rpm. The pH was then adjusted to 4.4 with a 10% aqueous phosphoric acid solution. During pH adjustment and the cooling step that followed pH adjustment, a coacervate formed from the gelatine and polyphosphate coated onto the oil droplets to form primary microcapsules, and then the primary microcapsules started to agglomerate to form lumps under agitation. A payload of 80% was obtained at this step.

Step B: A gelatine solution was prepared by dissolving 7.05 grams of gelatine 275 Bloom type A (isoelectric point of about 9) in 77.9 grams of deionized water under agitation at 70° C. until completely dissolved. 7.05 grams of beeswax melted at 70° C. was emulsified in the gelatine solution with a high speed Polytron™ homogenizer at 8,000 rpm for 4 minutes. A wax-in-water emulsion was formed. An alginate solution (45° C.) was prepared by dissolving 7.62 grams of sodium alginate in 630 grams of deionized water was added to the emulsion, and pH of the mixture was adjusted to 5.3 with 10% aqueous phosphoric acid. The mixture was then added into lump mixtures in step A under agitation at 450 rpm followed by adjusting the pH value of the mixture to 4.9, and cooling was carried out to cause the gelatine-alginate-wax composite material to form a coating onto the lumps formed in Step A to form microcapsules. Once the temperature had been lowered to 5° C., 3.8 grams of transglutaminase was added into the mixture to cross-link the shells. The mixture was then warmed up to room temperature and stirred at 600 rpm for 12 hours. Finally, the microcapsule suspension was spray dried to obtain a free-flowing powder. A final payload of 57% was obtained.

Example 6

Evaluation of Microcapsules

Figure 6:
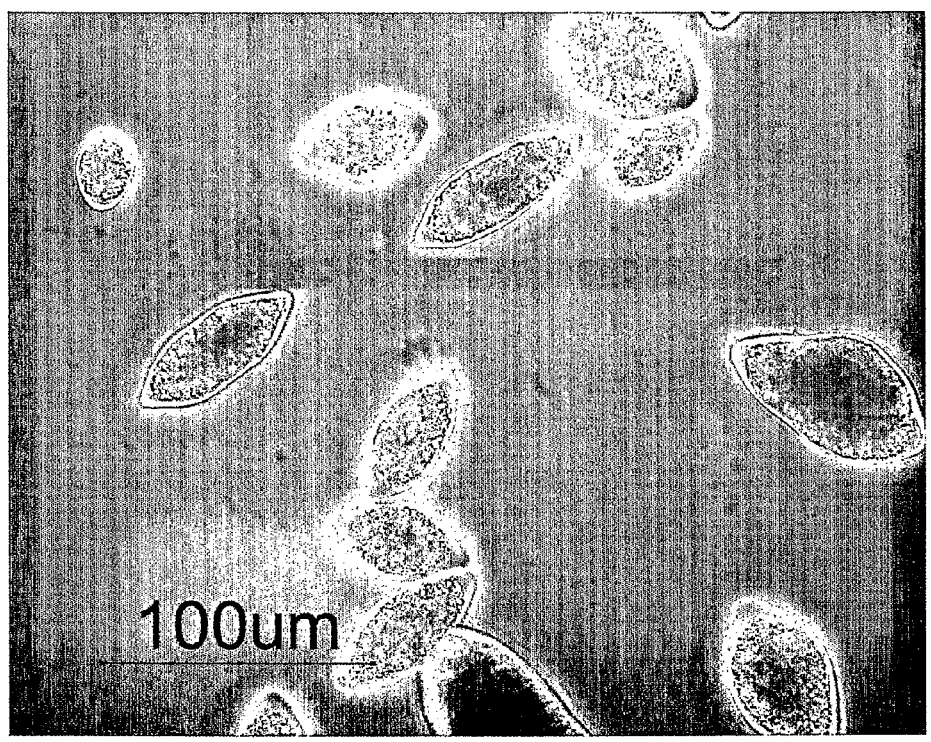
FIG. 6 is a photomicrograph of multi-core microcapsules prepared with a one-step process (62% payload), prepared for purposes of comparison.
Figure 7:
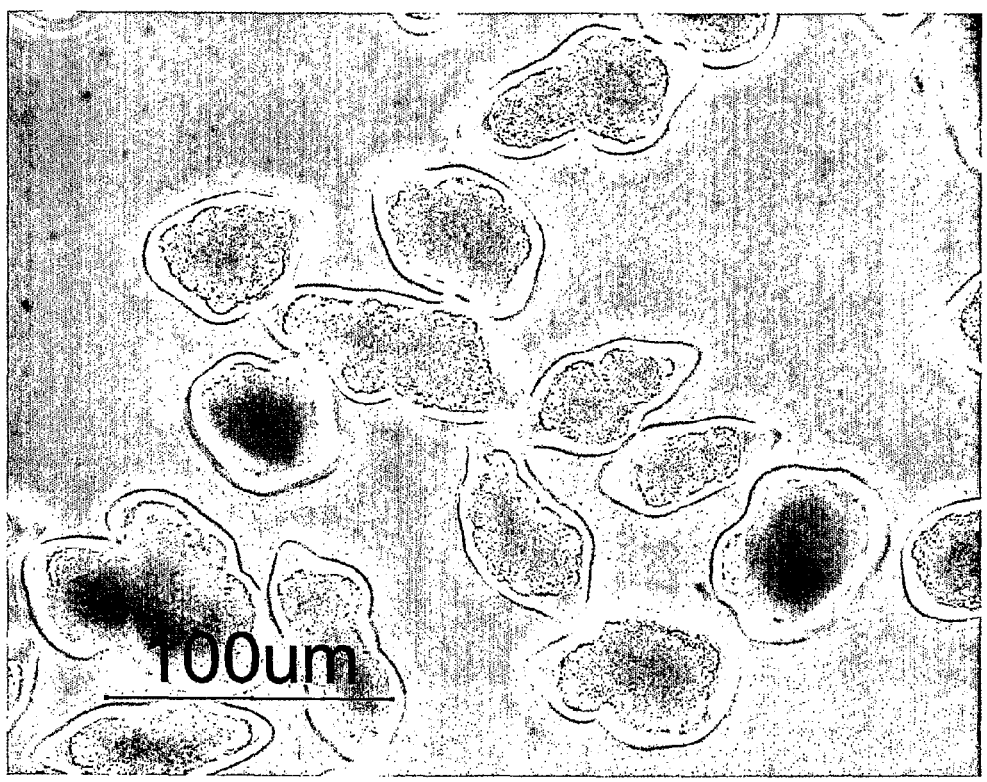
FIG. 7 is a photomicrograph of multi-core microcapsules prepared with a two-step process in accordance with the invention (59% payload).
Figure 8:
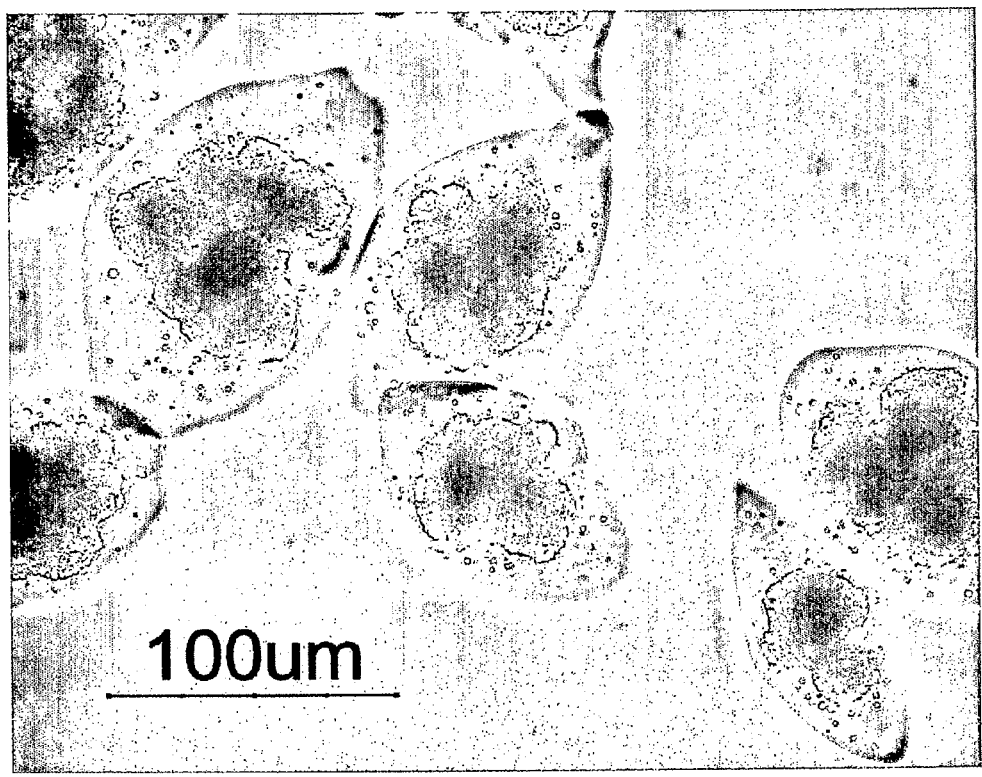
FIG. 8 is a photomicrograph of multi-core microcapsules prepared with a two-step process in accordance with the invention in which alginate is incorporated in the outer shell (53% payload).
Figure 9:
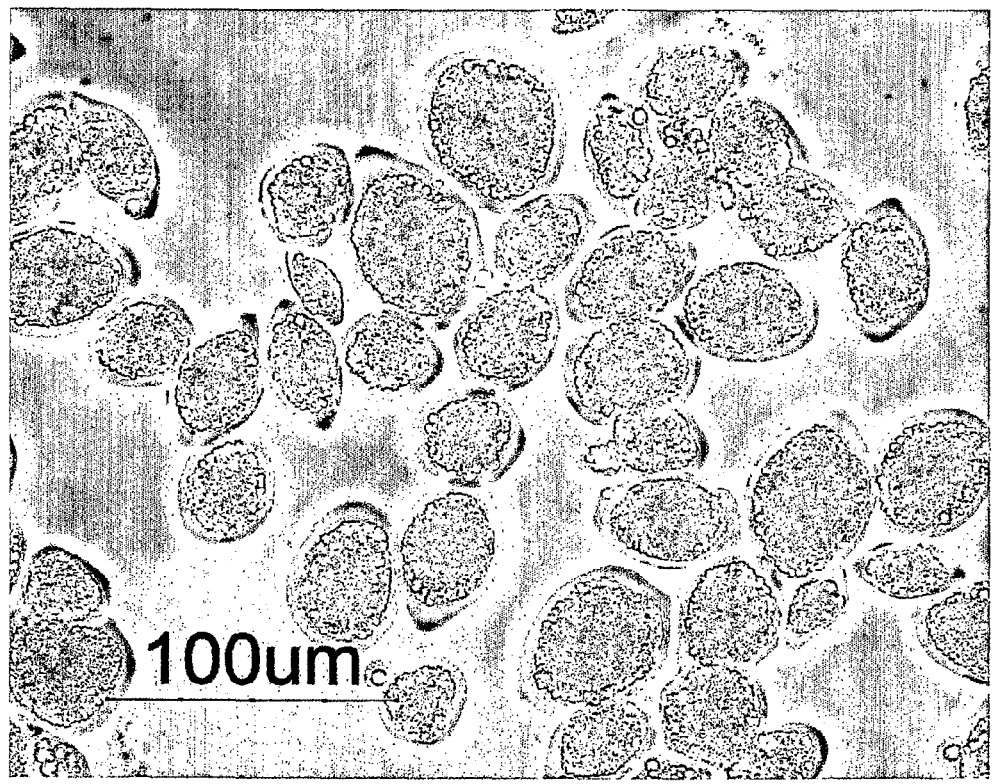
FIG. 9 is a photomicrograph of multi-core microcapsules prepared with a three-step process in which lipids and alginate are incorporated in an inner shell while gelatine and polyphosphate forms an outer shell.
Figure 10:
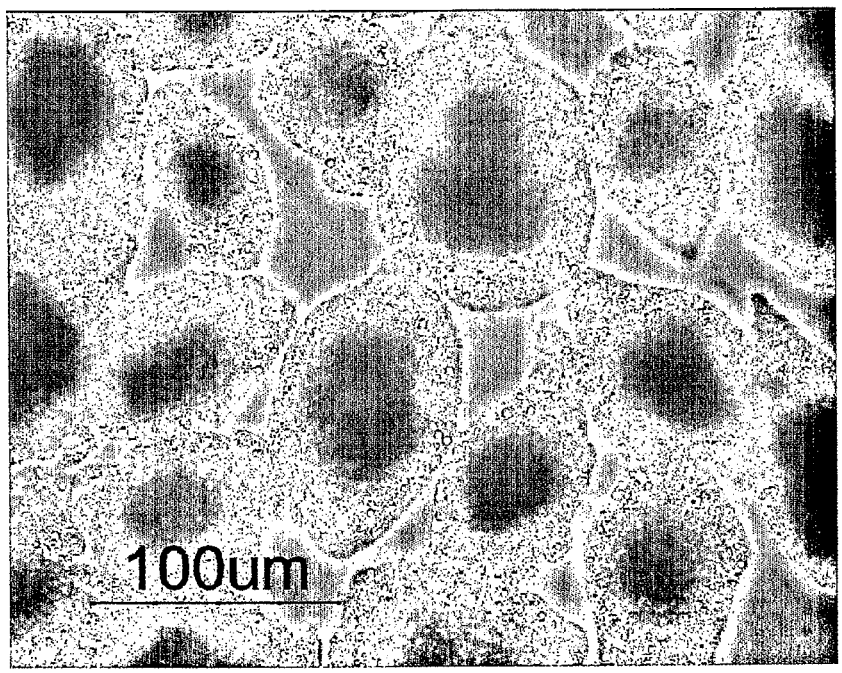
FIG. 10 is a photomicrograph of multi-core microcapsules prepared with a two-step process in which lipids and alginate are incorporated in the second shell.

Images of microcapsules of Examples 1-5 are shown in FIG. 6 to FIG. 10, respectively. It can be seen clearly that at approximately the same payload (60%) the microcapsules prepared with a two step process (FIG. 7) have much thicker outer shells than those prepared with one step process (FIG. 6). The microcapsules prepared with a three step process having a composite shell containing lipids (FIG. 9) clearly show the lipid droplets incorporated in the second shell and near the agglomerated oil core.

Accelerated oxidative stability in dry state was evaluated by placing the prepared microcapsule powders from each of Examples 1-4 in an oxygen bomb (Oxipres™, MIKROLAB AARHUS A/S, Denmark) with an initial oxygen pressure of 5 bar at a constant temperature of 65° C. When the encapsulated fish oil started to oxidize, the oxygen pressure dropped, and an induction period or time was determined. A longer induction period means that the contents of the microcapsules are better protected towards oxidation.

Induction periods are shown in Table 1. The microcapsules made from a two-step process in accordance with the invention have higher induction period (50-56 hours) than those made from a one-step process (41 hours). This translates to 22.0% to 37.6% increase in oxidative stability.

TABLE I

Comparison of the microcapsules described in Examples 1-5.

| Example # | Figure # | Description | Loading (%) | Induction period (hr) |
|---|---|---|---|---|
| 1 | 6 | Multicore one-step process for comparison | 62 | 41 |
| 2 | 7 | Two-step process with gelatine and polyphosphate in outer shell | 59 | 50 |
| 3 | 8 | Two-step process with alginate in outer shell | 53 | 55 |
| 4 | 9 | Three-step process incorporating wax and alginate in the second shell and gelatine and polyphosphate in the third shell | 52 | 44 |
| 5 | 10 | Two-step process incorporating wax and alginate in the shell | 57 | 56 |

All publications cited in this specification are herein incorporated by reference as if each individual publication were specifically and individually indicated to be incorporated by reference. The citation of any publication should not be construed as an admission that such publication is prior art.

Although the foregoing invention has been described in some detail by way of illustration and example for purposes of clarity of understanding, it is readily apparent to those of ordinary skill in the art in light of the teachings of this specification that certain changes or modifications may be made thereto without departing from the spirit or scope of the appended claims.

The invention claimed is:

1. A microcapsule consisting essentially of:
 (a) an agglomeration of primary microcapsules, each primary microcapsule comprising a loading substance and a first shell surrounding the loading substance;
 (b) a second shell surrounding said agglomeration; and
 (c) a third shell surrounding said second shell;
 wherein the first shell and second shell are formed from a complex coacervate between gelatin A and polyphosphate and the third shell is formed from a different complex coacervate, wherein the loading substance comprises at least 50% of the total mass of the microcapsule, and wherein the third shell comprises an antioxidant.

2. The microcapsule according to claim 1, wherein the third shell is formed from a complex coacervates comprising at least one polymer component selected from the group consisting of: a protein, a polyphosphate, a polysaccharide, gum arabic, alginate, chitosan, carrageenan, pectin, cellulose and cellulose derivatives.

3. The microcapsule according to claim 2, wherein the protein is selected from the group consisting of gelatine type A, gelatine type B, soy protein, whey protein, milk protein, and combinations thereof.

4. The microcapsule according to claim 1, further comprising at least one additional shell surrounding said third shell.

5. The microcapsule according to claim 4, wherein said at least one additional shell surrounding said third shell comprises is formed from a complex coacervate.

6. The microcapsule according to claim 1, wherein the second shell comprises an antioxidant.

7. The microcapsule according to claim 1, wherein at least one of the second and third shells comprises one or more hydrophobic components selected from the group consisting of waxes, oils, resins, and fats.

8. The microcapsule according to claim 1, wherein the third shell is cross-linked with an enzymatic cross-linker.

9. The microcapsule according to claim 1, having an exterior average diameter of from about 1 μm to about 2000 μm, and wherein said first shells have an average diameter of from about 40 nm to about 10 μm.

10. The microcapsule according to claim 1, wherein the loading substance comprises an omega-3 fatty acid, a derivative thereof, or mixture thereof.

11. The microcapsule according to claim 4, wherein at least one additional shell comprises one or more hydrophobic components selected from the group consisting of waxes, oils, resins, and fats.

* * * * *